United States Patent
Mercier et al.

(10) Patent No.: US 7,192,599 B2
(45) Date of Patent: Mar. 20, 2007

(54) MATTIFYING OIL-IN-WATER EMULSION

(75) Inventors: Michel F. Mercier, Mountainside, NJ (US); Paul Thau, Berkeley Heights, NJ (US); John A. Chase, Bedminster, NJ (US)

(73) Assignee: MMP, Inc., South Plainfield, NJ (US)

( * ) Notice: Subject to any disclaimer, the term of this patent is extended or adjusted under 35 U.S.C. 154(b) by 537 days.

(21) Appl. No.: 10/162,472

(22) Filed: Jun. 3, 2002

(65) Prior Publication Data

US 2003/0228334 A1    Dec. 11, 2003

(51) Int. Cl.
- A61K 9/107    (2006.01)
- A61K 7/02    (2006.01)
- A61K 7/42    (2006.01)
- A61K 33/06    (2006.01)

(52) U.S. Cl. ............... 424/401; 424/600; 424/682; 424/59; 514/938; 514/975

(58) Field of Classification Search ........... 424/401, 424/682, 600, 59; 514/938, 975
See application file for complete search history.

(56) References Cited

U.S. PATENT DOCUMENTS

| | | |
|---|---|---|
| 3,415,939 A | 12/1968 | Minton |
| 5,118,496 A | 6/1992 | Herstein |
| 5,215,759 A | 6/1993 | Mausner |
| 5,310,556 A | 5/1994 | Ziegler |
| 5,368,857 A | 11/1994 | Corcoran et al. |
| 5,382,432 A | 1/1995 | McCook et al. |
| 5,401,517 A | 3/1995 | Meyers et al. |
| 5,443,760 A | 8/1995 | Kasprzak |
| 5,476,661 A | 12/1995 | Pillai et al. |
| 5,534,265 A * | 7/1996 | Fowler et al. ............ 424/489 |
| 5,814,662 A | 9/1998 | Znaiden et al. |
| 5,902,591 A | 5/1999 | Herstein |
| 5,908,619 A | 6/1999 | Scholz |
| 5,916,548 A | 6/1999 | Hutchins et al. |
| 5,951,993 A | 9/1999 | Scholz et al. |
| 6,019,997 A | 2/2000 | Scholz et al. |
| 6,090,395 A | 7/2000 | Asmus et al. |
| 6,103,245 A | 8/2000 | Clark et al. |
| 6,197,319 B1 * | 3/2001 | Wang et al. ............ 424/401 |
| 6,277,893 B1 | 8/2001 | Babenko |
| 6,322,799 B1 | 11/2001 | Ilardi et al. |
| 6,323,246 B1 | 11/2001 | Nakama et al. |
| 6,333,042 B1 | 12/2001 | De La Charriere et al. |

* cited by examiner

*Primary Examiner*—Edward J. Webman
(74) *Attorney, Agent, or Firm*—Louis C. Paul

(57) ABSTRACT

The present invention relates to cosmetic and pharmaceutical oil-in-water emulsions which have a mattifying effect when applied to the skin. The invention comprises a hydrophilic, non-organically modified magnesium aluminum silicate or a bentonite clay and a polyol in the water phase; and a volatile, skin-compatible, lipophilic solvent and a high melting point lipophilic plasticizer in the oil phase. A preferred surfactant system to stabilize the emulsion includes non-toxic metal alkyl sulfates and/or sucrose esters.

25 Claims, No Drawings

MATTIFYING OIL-IN-WATER EMULSION

FIELD OF THE INVENTION

The present invention relates to topical cosmetic and pharmaceutical compositions. In particular, the invention relates to cosmetic and pharmaceutical emulsions which have a mattifying effect when applied to the skin.

BACKGROUND OF THE INVENTION

Prior art cosmetic compositions achieve mattification in several ways. Many are in the form of powders. Powders, however, often scatter resulting in uneven application and undesirable sternutatory effects (e.g., sneezing and eye reddening).

In response to uneven application and sternutatory effects of powders, other prior art mattifying compositions took the form of non-flowable creams and created a matte appearance by delivering magnesium aluminum silicate or bentonite clays in emulsions comprising high levels of volatile alcohols. See, e.g., U.S. Pat. No. 3,415,939 issued to Minton claiming a matte cosmetic cream composition with greater than 30% volatile alcohol content. In compositions of the type described by Minton, volatile alcohol quickly evaporates leaving behind mattifying ingredients. However, such compositions also have at least two significant drawbacks.

First, they often cause undesirable skin irritancy. In large part, the irritation is caused by the use of high levels of volatile alcohol, so much so that cosmetic products with high volatile alcohol content have generally fallen into disfavor among consumers and their use is now regulated in several states. Additionally, the type and levels of surfactants employed to maintain the stability of the compositions can indirectly cause irritation by disrupting the skin's outer lipid barrier, thus allowing irritants to penetrate the skin. Second, prior art emulsions comprising magnesium aluminum silicate as the mattifying ingredient often do not apply uniformly and tend to produce small splotches of residual whitening, which are aesthetically undesirable.

There has therefore long been a need for durable, cosmetic creams and lotions which can rapidly produce a uniform, matte appearance without creating irritation when applied to the skin. The emulsion of the present invention meets this need for non-irritating, non-whitening, mattifying compositions with desirable aesthetics and feel.

SUMMARY OF THE INVENTION

The claimed invention is a novel alcohol-free or low-alcohol, oil-in-water emulsion for application to the skin which imparts rapid, uniform and long-lasting mattification with desirable aesthetics and feel. The novel mattifying emulsion comprises a hydrophilic, non-organically modified magnesium aluminum silicate or a bentonite clay and a polyol in the water phase; and a volatile, skin-compatible, lipophilic solvent and a high melting point lipophilic plasticizer in the oil phase. Preferably, the surfactant system used to stabilize the emulsion includes non-toxic metal alkyl sulfates and/or sucrose esters.

DETAILED DESCRIPTION OF INVENTION

Emulsions are formed from at least two liquid phases, typically oil and water, which are immiscible in each other. The oil phase is comprised of ingredients which are substantially insoluble in water. Such water-insoluble ingredients are also described as lipophilic. In an oil-in-water emulsion, the inner oil phase is finely dispersed in the outer, continuous aqueous phase. Surface active ingredients, known as surfactants, are added to the emulsion to provide a uniform fine dispersion of the inner phase ingredients and to retard or prevent coalescence and eventual separation of the emulsion into its constituent phases.

The mattifying oil-in-water emulsion of the present invention is preferably alcohol-free, but may also comprise low levels of volatile alcohol. In both cases, the emulsions have an outer (aqueous) phase in which an inner (oil) phase is finely dispersed by gentle, skin-compatible surfactants. The emulsion comprises: a volatile, skin-compatible, lipophilic solvent; a high melting point lipophilic plasticizer; a hydrophilic, non-organically modified magnesium aluminum silicate or a bentonite clay; an emulsifier system; and a polyol. As detailed below, the aqueous phase preferably comprises: (i) from about 2% to about 6% by weight of a hydrophilic mattifying ingredient, which is either a hydrophilic, non-organically modified magnesium aluminum silicate or a bentonite clay; and (ii) from about 0.50% to about 5.0% by weight of a polyol, preferably from about 2% to about 3%. The oil phase comprises (i) from about 3% to about 30% by weight of a volatile, skin-compatible, lipophilic solvent, preferably from about 5% to about 25%, and most preferably from about 15% to about 20%; and (ii) from about 0.5% to about 6% by weight of a high melting point lipophilic plasticizer. In a preferred embodiment, the ratio of the high melting point lipophilic plasticizer to mattifying ingredient is approximately one to one.

The surfactant system of the present invention comprises from about 0.1% to about 2.0% by weight of the total composition, preferably from about 0.2% to about 1.0%. Preferred surfactants are non-toxic metal alkyl sulfates and/or sucrose esters.

A low-alcohol embodiment of the present invention comprises the above-described aqueous and oil phases and surfactant system, and additionally comprises from about 2% to about 5% by weight of $C_2$ and $C_3$ alcohols.

The aqueous phase of the emulsion of the present invention includes water, which is preferably deionized, distilled or similarly purified.

Mattifying ingredients suitable for use in compositions of the present invention are readily available. Preferred mattifying ingredients usable in the present invention include non-organically modified magnesium aluminum silicates and bentonite clays, with non-organically modified magnesium aluminum silicates being most preferred. One such magnesium aluminum silicate is sold under the tradename Matte Lite-239 by MMP, Inc., South Plainfield, N.J. Bentonite clays usable in the present invention include, for example, Bentonite USP brands manufactured by Whittaker Clark & Daniels of South Plainfield, N.J. or Polargel brands manufactured by American Colloid Company of Belle Fourche, S.D. Other mattifying ingredients which can be used in the present invention include hydrophobic starches, such as aluminum starch octenyl succinate, micronized zinc oxide, micronized titanium dioxide, kaolin, micas, and the like. A commercially available hydrophobic starch suitable for the present invention is marketed under the trade name Dry-Flo by National Starch & Chemical, Bridgewater, N.J. The mattifying effect of compositions of the present invention lasts from between about 3 hours to at least about 12 hours, depending on the oiliness of the skin. For oily skin, the duration of mattification is from about 3 hours to about 8 hours, preferably. For normal skin, the mattifying effect lasts from about 8 hours to about 12 or more hours, preferably.

Polyols available for use in compositions of the current invention are also widely available commercially and include, for example, glycerin and sorbitol. Preferred polyols are glycerin, propylene glycol, 1,3 butylene glycol or sorbitol. A more preferred polyol is glycerin. Other polyols which may be used in the present invention include hexylene glycol, polymeric polyols such as polypropylene glycol, and polyethylene glycol. Surprisingly, the polyol, in combination with the high melting point lipophilic plasticizer described below, allows for a more uniform mattification without the residual white splotches common in prior art compositions. Uniform matte appearance without whitening is especially important in color cosmetics and sunscreens.

Volatile, skin-compatible lipophilic solvents which can be used in the oil phase of the present invention include volatile silicones, such as cyclomethicone, isododecane, or mixtures thereof. Preferred cyclomethicones suitable for use in the invention are cyclopentasiloxane, cyclohexasiloxane, cycoltetrasiloxane or dimethicone (0.65 centistokes). A preferred isododecane usable in the present invention is sold under the tradename Permethyl 99A, by Presperse Inc., Piscataway, N.J.

As discussed above, low levels of volatile ethyl and, preferably, propyl alcohols may also be used in the invention. These alcohols provide a vehicle for carrying pharmaceutically active ingredients including, for example, salicylic acid, and also provide another means to modulate application properties.

The high melting point lipophilic plasticizer appears to coat or "plasticize" the surface of the non-organically modified magnesium aluminum silicate or bentonite clays, thus aiding in preventing the mattifying ingredients from being oxidized and thereby whitened. Solid fatty alcohols having from 14 to 30 carbon atoms per molecule may be used as the plasticizer in the present invention. Preferred fatty alcohols are from 16 to 22 carbon atoms per molecule in length. The most preferred fatty alcohols are preferred cetyl and cetearyl fatty alcohols. These fatty alcohols also provide a desirable semi-occlusive moisturizing action. Other plasticizers usable in the present invention include monodiglycerides, such as glycerol monostearate, and high-melting point esters, such as stearyl stearate, cetyl palmitate or behenyl stearate.

Preferred surfactants usable in the present invention include a non-toxic metal salt of an n-alkyl sulfate, a sucrose ester, or a combination of both. These surface active agents provide uniform dispersion and emulsification of the previously described lipophilic components. Alkyl sulfates suitable for use as surfactants in the present invention have from 12 to 22 carbon atoms per molecule. Preferred metals are sodium or potassium, with sodium as the most preferred. A preferred alkyl sulfate is sodium cetearyl sulfate. Preferred sucrose esters include sucrose stearate, sucrose oleate, sucrose laurate and isostearate. A more preferred sucrose ester is sucrose stearate, which is sold under the tradename Sisterna SP 70-C. A preferred surfactant system is about 0.25 % sucrose stearate by weight and about 0.25% by weight sodium cetearyl sulfate. Use of these preferred surfactants produces formulations with very desirable mildness characteristics.

Surprisingly, compositions containing the preferred sucrose esters described above as the sole emulsifier produced a less thixotropic composition than those also comprising alkyl sulfates. These unexpected improved flow characteristics allow the emulsion of the present invention to be more conveniently dispensed as a flowable lotion (e.g., in pumps) for easier application. For systems where greater fluidity and reduced viscosity is desired, a particularly preferred embodiment comprises about 0.50% by weight of sucrose stearate as the sole emulsifier.

Surfactants which are anionic, nonionic, cationic or amphoteric in character and combinations thereof can also be used in the present invention. Anionic-type surfactants may include fatty acid soaps, sodium lauryl sulfate, sodium lauryl ether sulfate, mono and dialkyl phosphates and sodium fatty acyl isothionate. Illustrative of the nonionic surfactants are alkoxylated compounds based upon fatty alcohols, fatty acids and sorbitan. Copolymers of polyoxypropylene-polyoxyethylene, sold under the Pluronic tradename by BASF Corp., Mount Olive, N.J., as well as non-ethoxylated, nonionic emulsifiers, such as sucrose laurate, sucrose oleate, alkyl polyglucosides, polyglyceryl-4 palmitate, polyglyceryl-10laurate can be utilized. Amphoteric surfactants suitable for use in the invention include dialkylamine oxide and betaines, such as cocoamido propyl betaine.

Compositions of the present invention exhibit long-lasting, uniform mattification, without whitening, and can be used as a vehicle for a variety of products in which an oil-in-water vehicle is appropriate. The invention can therefore be employed in a wide range of cosmetic and pharmaceutical products, including, but not limited to, matte make-up compositions, oil absorbing face masks, matte anti-acne oil absorption vehicles, matte after shave balms or lotions, fragrance delivery vehicles, sunscreens, foot creams, and other dermatologic vehicles.

In order to produce the desired products, the basic components of the invention described above may be combined with other cosmetic and pharmaceutical ingredients which are well known to cosmetic and pharmaceutical chemists. Examples of such additional components include, but are not limited to, antiseborrheic agents, anti-acne agents, antioxidants, skin lightening agents, depigmenting agents, anti-wrinkle agents, vitamins, sunscreen agents, self-tanning agents, topical analgesics, anti-inflammatory agents, anti-pruritic agents deodorants, as well as purely cosmetic ingredients, such as pigments, water soluble emollients, humectants, stabilizers and fragrances. Sunscreen agents which do not whiten are most suitable for use in the present invention and include micronized titanium dioxide, micronized zinc oxide or avobenzone which is commercially available under the tradename Parsol 1789. Preferred pigments in makeup emulsions of the present invention are iron oxides and titanium dioxides.

The oil-in-water emulsion of the present invention is prepared according to principles and techniques generally known to those skilled in the cosmetic and pharmaceutical arts. Ingredients which are miscible (e.g., disodium EDTA or other chelating agent) or dispersible (e.g., hydrophilic mattifying ingredient) in the water phase are mixed together with propeller agitation. In order to accelerate hydration of the mattifying ingredient, the above mixture is preferably heated to a temperature of about 60° C. and processed with a high speed homogenizer. It is preferable to hydrate non-organically modified magnesium aluminum silicate with a Silverson L4RT homogenizer (manufactured by A. Silverson Machines, Ltd., Chesham, England) operating at 5500–6500 rpm for about ten minutes at about 60° C. Other mixers such as a colloid mill or propeller mixer may also be used, although the latter would considerably increase processing time. A colloid mill with a narrow orifice may be preferred when adding high pigments loads.

Polyol, emulsifier (i.e., non-toxic metal alkyl sulfate and/or sucrose ester) and high melting point lipophilic plasticizer (e.g., cetyl alcohol) are then added to the above water phase mixture. It is preferable to incorporate these ingredients while mixing with medium propeller agitation and heating until a temperature is reached at which the emulsifiers melt, typically from about 65° C. to about 85° C. The speed of propeller mixing should be sufficient to create a vortex but not so fast as to cause aeration. Alternatively, the emulsifier and plasticizer may be melted in separate vessels and mixed with the polyol and other water phase ingredients using a rotating static mixer, a colloid mill, or an in-line homogenizer.

The emulsion is then allowed to cool to about 55° C. while being further mixed with a high speed homogenizer, at which point the volatile, skin-compatible, lipophilic solvent (e.g., cyclomethicone) is added. Low levels of volatile ethyl and/or propyl alcohol may also be added at this stage of processing. Mixing with the homogenizer continues until viscosity begins to build up, normally about 50° C. At this point, it is preferable to switch to a medium paddle or side-sweep mixer in order to remove air that may have been incorporated during homogenization. Once the mixture has cooled down further, to about 45° C., preservatives as well as any water lost through evaporation may be added. Fragrance and other temperature sensitive active ingredients may also be added once the emulsion is below about 45° C. Sweep mixing and cooling are continued, preferably until about 32° C., at which time processing is stopped.

Homogenizers, mixers and mills which are suitable for use in the process described above are well known to artisans of ordinary skill in the art.

The invention is further illustrated by the following examples, which are intended to illustrate and not limit the invention.

EXAMPLE 1

Mattifying Facial Vehicle

A mattifying oil-in-water emulsion cosmetic composition having the formula:

|  | % w/w |
| --- | --- |
| Deonized Water | 76.25 |
| Disodium Ethylenediamine-tetraacetate (EDTA) | 0.10 |
| Magnesium Aluminum Silicate | 3.00 |
| Glycerin | 2.00 |
| Sucrose Stearate | 0.25 |
| Sodium Cetearyl Sulfate | 0.25 |
| Cetyl Alcohol | 3.00 |
| Cyclomethicone | 15.00 |
| Preservative | 0.15 |

The above described vehicle for producing a matte facial appearance with no whitening was made according to the following procedure: The aqueous phase of the emulsion was prepared by combining deionized water, disodium EDTA, and magnesium aluminum silicate in a mixing vessel with medium prop agitation while heating for approximately 30 to 45 minutes. At 60° C., mixing was continued for about 30 to 45 minutes in a homogenizer until the magnesium aluminum silicate was hydrated thoroughly. Mixing with medium prop agitation while heating was then resumed and the polyol, glycerin, was added followed by the surfactants, sucrose stearate and sodium cetearyl sulfate. Next, the high melting point lipophilic plasticizer, cetyl alcohol, was added and melted within the vessel. Heating continued until a temperature of 70 to 75° C. was reached, at which point heating was stopped. The emulsion was then homogenized at 6000 to 7000 rotations per minute until the temperature cooled to 55° C. at which point the volatile, lipophilic solvent, cyclomethicone, was added. Mixing with the homogenizer was stopped at the earlier of 50° C. or when viscosity build-up was observed. Sweep mixing was then started and the emulsion was cooled. At 45° C., preservatives as well as any water lost through evaporation were added. Sweep mixing and cooling were continued until 32° C., at which time processing was stopped.

The mattifying facial vehicle of Example 1 was a white, opaque lotion. This emulsion was stable at 40° C. for more than two months, at room temperature for more than six months, and after three freeze/thaw cycles.

EXAMPLE 2

Mattifying Facial Vehicle

A mattifying facial vehicle was made according to the same procedure as in Example 1. Example 2 differs from Example 1 in that the surfactant used was sucrose stearate. The viscosity of Example 2 was lower than Example 1, and resulted in a more fluid and flowable product.

|  | % w/w |
| --- | --- |
| Deionized Water | 76.25 |
| Disodium EDTA | 0.10 |
| Magnesium Aluminum Silicate | 3.00 |
| Glycerin | 2.00 |
| Sucrose Stearate | 0.50 |
| Cetyl Alcohol | 3.00 |
| Cyclomethicone | 15.00 |
| Preservative | 0.15 |

The mattifying facial vehicle of Example 2 was a white, opaque, free-flowing lotion. This emulsion was stable at 40° C. for more than two months, at room temperature for more than six months, and after three freeze/thaw cycles.

EXAMPLE 3

Mattifying Mask

A mattifying mask was made according to the same procedure as described above in Example 1.

|  | % w/w |
| --- | --- |
| Deionized Water | 71.91 |
| Disodium EDTA | 0.10 |
| Magnesium Aluminum Silicate | 5.00 |
| Glycerin | 2.00 |
| Sucrose Stearate | 0.42 |
| Sodium Cetearyl Sulfate | 0.42 |
| Cetyl Alcohol | 5.00 |
| Cyclomethicone | 15.00 |
| Preservative | 0.15 |

The mattifying mask of Example 3 was an aesthetically rich looking white, opaque cream. This emulsion was stable at 40° C. for more than two months, at room temperature for more than six months, and after three freeze/thaw cycles.

EXAMPLE 4

Mattifying Fragrance Vehicle

A mattifying fragrance delivery vehicle was made according to the same procedure as described above in Example 1, except that fragrance was added at the same time as the preservatives.

|  | % w/w |
| --- | --- |
| Deionized Water | 74.25 |
| Disodium EDTA | 0.10 |
| Magnesium Aluminum Silicate | 3.00 |
| Glycerin | 2.00 |
| Sucrose Stearate | 0.25 |
| Sodium Cetearyl Sulfate | 0.25 |
| Cetyl Alcohol | 3.00 |
| Cyclomethicone | 15.00 |
| Preservative | 0.15 |
| Fragrance | 2.00 |

The mattifying fragrance vehicle of Example 4 was a fragrant, white, opaque lotion. This emulsion was stable at 40° C. for more than two months, at room temperature for more than six months, and after three freeze/thaw cycles.

EXAMPLE 5

Mattifying Makeup Vehicle

A mattifying makeup delivery vehicle was made according to the same procedure as described above in Example 1, except as follows: After the water-surfactant-plasticizer emulsion was homogenized from 6000–7000 rpm and cooled to 60–65° C., the pigments (i.e., titanium dioxide, iron oxides) were added. Nylon 12 was also at that time. At 55° C., cyclomethicone was added and the procedure described above was continued through the end of processing.

|  | % w/w |
| --- | --- |
| Deionized Water | 73.25 |
| Disodium EDTA | 0.10 |
| Magnesium Aluminum Silicate | 3.00 |
| Glycerin | 2.00 |
| Sucrose Stearate | 0.25 |
| Sodium Cetearyl Sulfate | 0.25 |
| Cetyl Alcohol | 3.00 |
| Titanium Dioxide | 2.00 |
| Red Iron Oxide | 0.20 |
| Yellow Iron Oxide | 0.50 |
| Black Iron Oxide | 0.05 |
| Nylon-12 | 0.25 |
| Cyclomethicone | 15.00 |
| Preservative | 0.15 |

The mattifying makeup vehicle of Example 5 was a pigmented opaque cream. This emulsion was stable at 40° C. for more than one and one-half months, at room temperature for more than two months, and after three freeze/thaw cycles.

We claim:

1. A mattifying oil-in-water emulsion composition suitable for application to the skin comprising:

(a) from about 3% to about 30% by weight of a volatile, skin-compatible, lipophilic solvent;

(b) from about 0.5% to about 6% by weight of plasticizer selected from the group consisting of solid fatty alcohols having from 14 to 30 carbon atoms per molecule, monodiglycerides, stearyl stearate, cetyl palmitate, and behenyl stearate;

(c) from about 2% to about 6% by weight of a hydrophilic, non-organically modified magnesium aluminum silicate or a bentonite clay;

(d) from about 0.1% to about 2.0% by weight of the total composition of a surface active agent; and (e) from about 0.50% to about 5.0% by weight of the total composition of a polyol.

2. A composition according to claim 1 wherein the volatile, skin-compatible, lipophilic solvent is one or more substances selected from the group consisting of volatile silicones, isododecane, or mixtures thereof.

3. A composition according to claim 2, wherein the volatile, skin-compatible, lipophilic solvent is one or more of cyclomethicone (cyclopentsiloxane, cyclohexasilixane, cycoltetrasiloxane) or dimethicone (0.65 centistokes).

4. A composition according to claim 1 wherein the plasticizer is a solid fatty alcohol having from 14 to 30 carbon atoms per molecule.

5. A composition according to claim 1 wherein the plasticizer is a solid fatty alcohol from 16 to 22 carbon atoms per molecule.

6. A composition according to claim 1 wherein the plasticizer is cetyl alcohol or cetearyl alcohol.

7. A composition according to claim 1 wherein the plasticizer is a monodiglyceride.

8. A composition according to claim 1 wherein the plasticizer is stearyl stearate, cetyl palmitate, or behenyl stearate.

9. A composition according to claim 1 wherein the polyol is selected from a group comprising glycerin, propylene glycol, 1,3 butylene glycol or sorbitol.

10. A composition according to claim 1 wherein the polyol is glycerin.

11. A composition according to claim 1 wherein the polyol is from about 2% to about 3% by weight of the total composition.

12. A composition according to claim 1 wherein the surface active ingredient(s) is from about 0.2% to about 1.0% by weight of the total composition.

13. A composition according to claim 1 wherein the surface active ingredient is a non-toxic metal salt of an n-alkyl sulfate, having from 12 to 22 carbon atoms per molecule, or a sucrose ester, or a combination of said n-alkyl sulfate and a sucrose ester.

14. A mattifying oil-in-water emulsion composition according to claim 1 further comprising an ethyl or propyl alcohol, or mixtures thereof, from about 2% to about 5% by weight of the total composition.

15. A composition according to claim 14 wherein the volatile alcohol is an ethyl alcohol.

16. A mattifying oil-in-water emulsion composition suitable for application to the skin comprising:

(a) from about 3 to about 30% by weight of a volatile, skin-compatible, lipophilic solvent;

(b) from about 0.5% to about 6% by weight of plasticizer selected from the group consisting of solid fatty alcohols having from 14 to 30 carbon atoms per molecule, monodiglycerides, stearyl stearate, cetyl palmitate, and behenyl stearate;

(c) from about 2% to about 6% by weight of a hydrophilic, non-organically modified magnesium aluminum silicate or a bentonite clay;

(d) from about 0.1% to about 2.0% by weight of the total composition of sucrose stearate or sucrose stearate in combination with sodium cetearyl sulfate; and (e) from about 0.50% to about 5.0% by weight of the total composition of a polyol.

17. A composition according to claim 16 wherein the sucrose stearate or sucrose stearate in combination with sodium cetearyl sulfate is from about 0.2% to about 1.0% by weight of the total composition.

18. A method of producing a matte appearance on skin, comprising applying the composition of claim 1 to the skin.

19. A method of cosmetically treating skin, comprising applying the composition of claim 1 to the skin.

20. A composition according to claim 1 which is a makeup.

21. A composition according to claim 1 which is a mask.

22. A composition according to claim 1 which is a vehicle for delivering fragrance.

23. A composition according to claim 1 which is a vehicle for delivering ingredients to treat oily or blemished skin.

24. A composition according to claim 1 which is a sunscreen.

25. A composition according to claim 1 which is an aftershave.

* * * * *